(12) United States Patent
Gupta

(10) Patent No.: US 11,559,483 B2
(45) Date of Patent: Jan. 24, 2023

(54) NASAL FOAM VIA CRIBRIFORM PLATE FOR MEDICATION DELIVERY TO THE BRAIN AND/OR BODY AND FOR NASAL MOISTURIZATION AND HYGIENE

(71) Applicant: Sanjay Gupta, Voorhees, NJ (US)

(72) Inventor: Sanjay Gupta, Voorhees, NJ (US)

( * ) Notice: Subject to any disclaimer, the term of this patent is extended or adjusted under 35 U.S.C. 154(b) by 0 days.

(21) Appl. No.: 15/205,611

(22) Filed: Jul. 8, 2016

(65) Prior Publication Data
US 2017/0007540 A1    Jan. 12, 2017

Related U.S. Application Data

(60) Provisional application No. 62/269,348, filed on Dec. 18, 2015, provisional application No. 62/191,147, filed on Jul. 10, 2015.

(51) Int. Cl.
| | |
|---|---|
| *A61K 9/00* | (2006.01) |
| *A61K 47/46* | (2006.01) |
| *A61K 47/02* | (2006.01) |
| *A61K 9/12* | (2006.01) |
| *A61K 8/04* | (2006.01) |
| *A61M 31/00* | (2006.01) |
| *A61K 8/96* | (2006.01) |
| *A61Q 19/10* | (2006.01) |

(52) U.S. Cl.
CPC ............ *A61K 9/0043* (2013.01); *A61K 8/046* (2013.01); *A61K 8/965* (2013.01); *A61M 31/002* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 5,853,618 A | * | 12/1998 | Barker | C09K 3/30 |
| | | | | 252/179 |
| 8,283,160 B2 | * | 10/2012 | Frey, II | A61K 35/30 |
| | | | | 424/93.7 |
| 2007/0119451 A1 | * | 5/2007 | Wang | A61M 15/0028 |
| | | | | 128/203.15 |
| 2008/0054099 A1 | * | 3/2008 | Giroux | B05B 7/0869 |
| | | | | 239/337 |
| 2008/0241271 A1 | | 10/2008 | Roman et al. | |
| 2010/0016267 A1 | * | 1/2010 | Theeuwes | A61K 9/0043 |
| | | | | 514/172 |
| 2011/0207822 A1 | | 8/2011 | Lopes | |
| 2013/0142868 A1 | | 6/2013 | Hoekman et al. | |
| 2014/0242064 A1 | * | 8/2014 | Morriss | A61K 9/0043 |
| | | | | 424/94.67 |

FOREIGN PATENT DOCUMENTS

| | | | | |
|---|---|---|---|---|
| GB | 2338649 | * | 12/1999 | A61K 9/00 |
| WO | WO-2012156317 A2 | * | 11/2012 | A61K 9/0043 |

OTHER PUBLICATIONS

Frey, Drug Devel. Deliv., 2(5) (2008) (Year: 2008).*
Hansen et al., BMC Neuroscience 2008, 9(Suppl 3):S5 (2008) (Year: 2008).*
Miyake et al., Am. J.Rhinol. Allergy, 29:124-127 (2015) (Year: 2015).*
Meredith et al., AAPS J., 17(4):780-787 (2015) (Year: 2015).*
Shinde et al., Indo. Am. J. Pharma. Res., 3(12):1322-1327 (2013) (Year: 2013).*
Pardeshi et al., Exp. Op. Drug Deliv., 10(7):957-972 (2013) (Year: 2013).*
Djupesland et al., Ther. Deliv., 5(6):709-733 (2014) (Year: 2014).*
C. Andrade, Intranasal Drug Delivery in Neuropsychiatry: Focus on Intranasal Ketamine for Refractory Depression, J. Clin. Psychiatry, 2015;76(5):e628-e631.

* cited by examiner

*Primary Examiner* — David W Berke-Schlessel
(74) *Attorney, Agent, or Firm* — Jonathan D. Ball; Greenberg Traurig, LLP

(57) ABSTRACT

Methods and compositions for delivering medicine and other substances to the brain and the body via the cribriform plate using foamable compositions are described. Methods and compositions for improving nasal hygiene and moisturizing the nasal cavity using foamable compositions are also described.

9 Claims, 4 Drawing Sheets

NASAL FOAM VIA CRIBRIFORM PLATE FOR MEDICATION DELIVERY TO THE BRAIN AND/OR BODY AND FOR NASAL MOISTURIZATION AND HYGIENE

CROSS REFERENCE TO RELATED APPLICATIONS

The present application claims the benefit of U.S. Provisional Patent Application No. 62/191,147 filed Jul. 10, 2015 and U.S. Provisional Patent Application No. 62/269,348 filed Dec. 18, 2015, the entire disclosures of which are hereby incorporated by reference herein.

BACKGROUND OF THE INVENTION

Delivering medications and other substances to the brain is very desirable for CNS active drugs but extremely challenging. Even if a medication is injected into the bloodstream, e.g., intravenously, it may not cross the barrier between blood and brain called the blood brain barrier. Also, many medications can be destroyed by blood and thus preferred to be given directly to the brain. Giving the medications via the oral route creates a further barrier of absorption and metabolism by stomach gut and liver, before the medications reach the blood. So all these methods reduce the percentage of actual medication that will reach the brain if at all and also slows the time of action. This leads to taking an extra dose of medication for the same results, which in turn causes an increase in side effect profile.

A mechanism of direct brain delivery via cribriform plate, thus bypassing the blood brain barrier, gut and liver is desirable. The cribriform plate is a porous plate of bone located between brain and nose in the roof of nasal cavity that has holes through which nerves and blood vessels pass through between nose and brain. Medications/chemicals and substances can reach the brain from the nose through these same holes. This allows for a larger percentage of an active substance to be transported to the brain or bloodstream at a much faster rate compared to other modes of delivery, including intravenous, oral or other methods.

The way to reach the cribriform plate is via the nasal cavity. Current modes of medication or substance delivery through the nasal cavity include nasal sprays, mists, aerosols, and liquid and gel formulations. One problem with current modes of nasal delivery is that they are unable to reach the back part of the roof of the nasal cavity, where the cribriform plate is located. Another problem is that the contact period of such substances with the nasal cavity is minimal, and therefore the time period for transport, i.e., absorption into the bloodstream or brain, is decreased. This leads to less absorption of the drug in the nasal cavity or body and substantially reduced efficacy of the drug. It would therefore be desirable to have a substance delivery method and composition that is able to fill the entire nasal cavity and reach the roof of the nasal cavity and that has a longer contact period with the nasal mucosa. Another problem with the liquid, spray and gel form is dripping into the throat that not only wastes medicine and drugs but is uncomfortable to the patient and can cause choking.

BRIEF SUMMARY OF THE INVENTION

The disclosed embodiments are generally directed to methods and compositions for delivering medicine and other substances to the brain via the cribriform plate located in the back part of the roof of the nose (or olfactory part of the nasal cavity) using foam compositions. These methods and compositions can also be used to deliver drugs to the rest of the body besides the brain and for improving nasal hygiene and moisturization using foam compositions. These methods and compositions can also be used for local nasal and sinus applications for various chemicals/medications/substances.

The foam composition may comprise a base solution along with a propellant gas or air. The base solution may be mixed with the propellant gas or air at the time of delivery, prior to delivery or after delivery to the target area. The base solution may include, for example various compositions of water, salt, fat, milk, oil, proteins and other substance or various combinations of some or all of the constituents. It may also include the medicine, chemicals, stem cells, hormones, peptides or other substances to be delivered. Other additions to this base solutions formula may include various surfactants, foaming agents, stabilizing agents, pH modifying agents, osmolarity modifying agents, moisturizing agents and preservatives. More modification can be done by adding absorption enhancing agents and a variety of other agents. All the substances or medicine in the base solution can be of varying sizes including nano particles of less than 1 nanometer to more than 2000 nanometers.

The foaming agents can be single or mixed product of several surfactants and may include, for example, various compositions of sodium lauryl ether sulfate (SLES), sodium lauryl sulfate (also known as sodium dodecyl sulfate or SDS) and ammonium lauryl sulfate (ALS). Nitrous oxide, air, $CO_2$ or other gaseous products may be used to create bubbles in the foam composition, allowing substances to fill the entire nasal cavity with an increased contact period. To make the foam after the medicine or substance has been delivered, the medicine or drugs can be applied to the target area first in a powdered, dry or gas treated dry powder form and then the base solution can be propelled with gas or air to the target area forming the foam of the medicinal powder at the target area.

Moisturizing agents may include, for example, glycerin, aloe vera, hyaluronan, shea butter, milk fat, or oil, including but not limited to olive oil, coconut oil, flaxseed oil, avocado oil or almond oil.

In addition to a vehicle for medicine delivery to the brain via the cribriform plate or to the body via the nasal cavity, these methods may also be used to moisturize the nasal cavity or to clean the nasal cavity for better hygiene, making it extremely useful for people working in dusty, dry, and polluted environments. At present, nasal hygiene methods include sprays and liquid compositions, which have the problems of reaching only a partial area of the nose, minimal contact time with the nasal cavity, dripping in the throat causing discomfort to the patients and possible choking hazard. Although specific examples of novel foam compositions are included herein, any foam composition may be used for the nasal hygiene improvement, and nasal moisturization methods described.

In one embodiment, a method of delivering a foamable pharmaceutical composition to the cribriform plate of a nasal cavity of a subject is provided comprising generating a biologically active foam composition sufficient to deliver at least 50% of an active agent across a blood brain barrier of the subject and delivering the biologically active agent foam composition to the cribriform plate of the nasal cavity, wherein the biologically active foam composition comprises an active agent selected from the group consisting of a stem cell, an antimicrobial agent, an antineoplastic agent, an antiarrhythmic agent, an antihypertensive agent, an analgesic agent, anti-inflammatory agent, an anticonvulsant, an anti-Parkinson's agent, a sedative, a muscle relaxant, an anticoagulant, a hormone modulator, an immunosuppressive agent, a metabolic agent, an anesthetic, a nutritional supplement, an antidepressant, a radiologic agent, and an antimigraine agent, and a stabilizing agent.

In another embodiment, a method for delivering a foamable saline solution for cleansing and hydrating the nasal cavity is provided.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
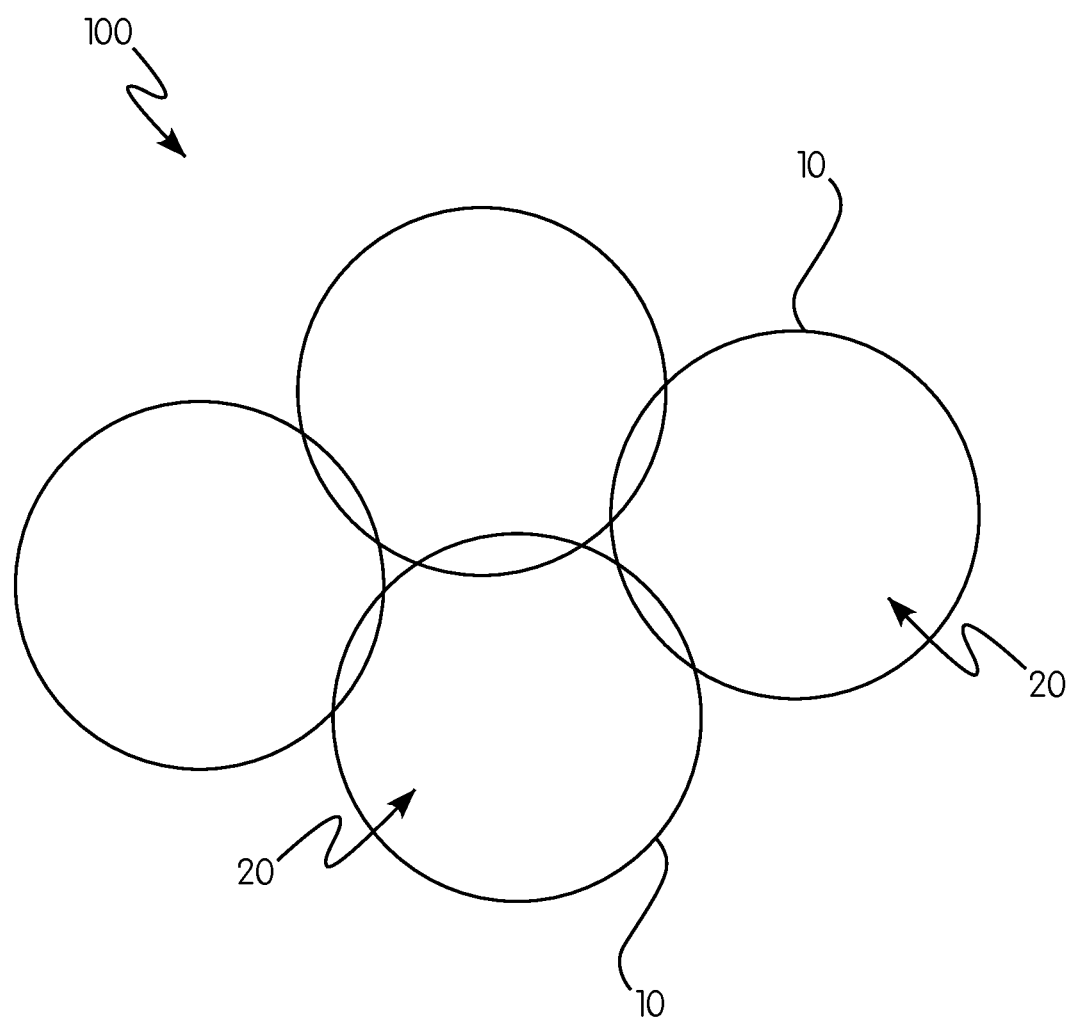
FIG. 1 illustrates an example of a foam composition in accordance with an aspect of the present invention in a magnified view.

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the identified element and designated parts thereof. Additionally, the term "a," as used in the specification, means "at least one." The terminology includes the words noted above, derivatives thereof and words of similar import.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Active agent" as used herein refers to any medication or substance having a therapeutic effect on a subject.

As used herein, the terms "foam" and "foam composition" are meant to encompass complete and partial foam compositions.

Furthermore, the described features, advantages and characteristics of the embodiments of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

FIG. 1 illustrates an example of a foam composition 100 in magnified view, in which one or more disclosed embodiments may be implemented. In one embodiment, the foam composition 100 comprises an active agent 10, i.e. medicine or other substance and a gas 20. The foam composition 100 may deliver the active agent 10, to the brain or body via the cribriform plate area of the nose.

Figure 2:
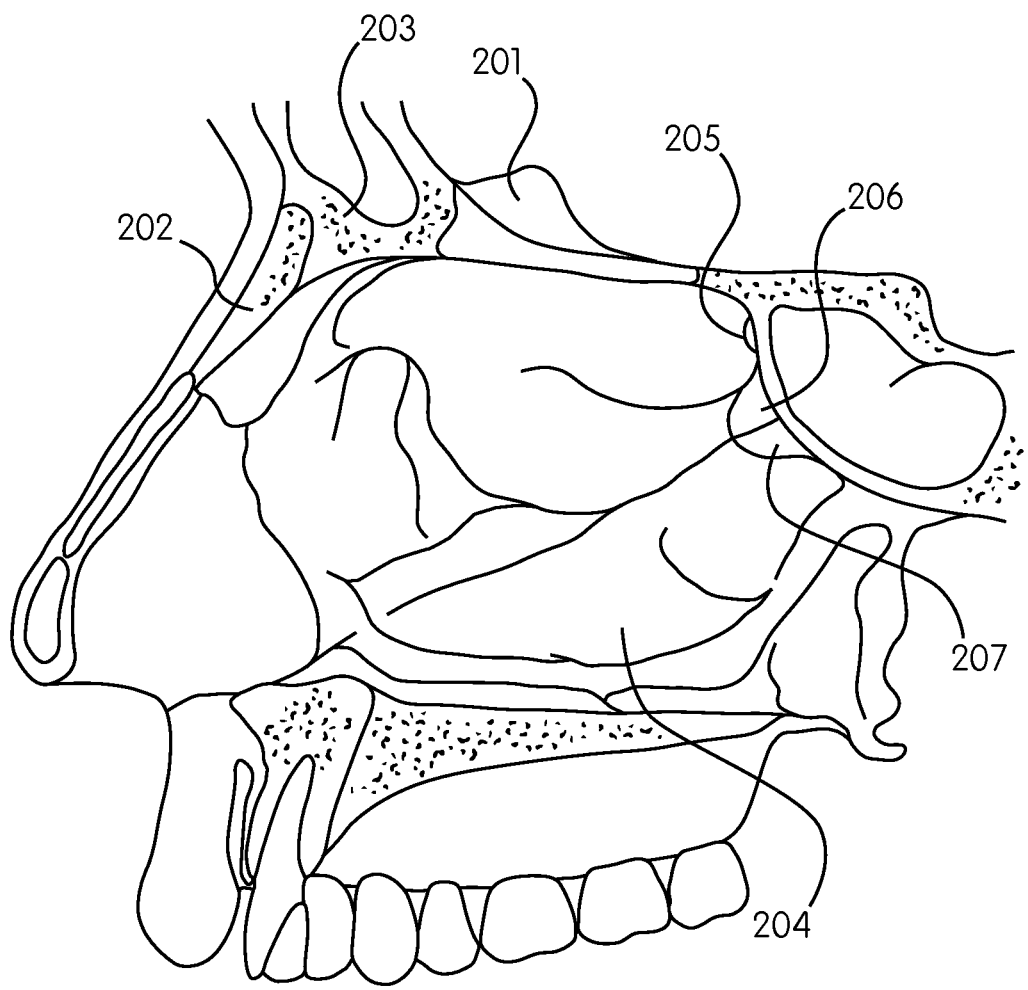
FIG. 2 illustrates a cross-sectional view of nose including the location of the cribriform plate in the roof of the nose.

FIG. 2 shows the roof of the nasal cavity formed by the cribriform plate 201, nasal bones 202, nasal spine of the frontal bone 203, vomer 204, opening of the sphenoidal sinus 205, ala of vormer 206 and sphenoidal rostrum 207.

Any medication or chemical substance can be delivered through the nasal mucosa, including the ones whose target and function are directly in the brain, as the cribriform plate area provides a direct route to the brain without passing through the gut, liver, or blood brain barrier. Such medications may include but are not limited to several lifesaving medications e.g., those used to treat seizures, drug overdose or addiction, e.g., naloxone, buprenorphine and midazolam, headache and migraine, e.g., triptans, excessive sedation, e.g. caffeine or nicotine, depression, and brain tumors, pain medications, vaccines, stem cells, hormones like glucagon, insulin and oxytocin, and Alzheimer's disease, e.g., insulin, nicotine, and vitamins.

Examples of an active agent include but are not limited to: a stem cell, a genetically modified stem cell, an anti-infective, an amebicide, an aminoglycoside, an anthelmintic, an antifungal, an azole antifungal, an echinocandin, a polyene, an antimalarial agent, an antimalarial quinolone, an antituberculosis agent, an aminosalicylate, a diarylquinoline, a hydrazide derivative, a nicotinic acid derivative, a rifamycin derivative, a streptomyces derivative, an antiviral agent, an adamantane antiviral, an antiviral booster, an antiviral interferon, a chemokine receptor an antagonist, an integrase strand transfer inhibitor, a neuraminidase inhibitor, a NNRTI, a NS5A inhibitors, a nucleoside reverse transcriptase inhibitor (NRTI), a protease inhibitor, a purine nucleoside, a carbapenem, a cephalosporin, a cephalosporin/beta-lactamase inhibitor, a first generation cephalosporin, a fourth generation cephalosporin, a next generation cephalosporin, a second generation cephalosporin, a third generation cephalosporin, a glycopeptide antibiotics, a glycylcycline, a leprostatic, a lincomycin derivative, a macrolide derivative, a ketolide, a macrolide, an oxazolidinone antibiotic, a penicillin, an aminopenicillin, a antipseudomonal penicillin, a beta-lactamase inhibitors, a natural penicillin, a penicillinase resistant penicillin, a quinolone, a sulfonamide, a tetracycline, a urinary anti-infective, an antineoplastic, an alkylating agent, an anti-CTLA-4 monoclonal antibody, an antibiotic/antineoplastic, an antimetabolite, an antineoplastic detoxifying agent, an antineoplastic interferon, a BCR-ABL tyrosine kinase inhibitor, a CD20 monoclonal antibody, a CD30 monoclonal antibody, a CD33 monoclonal antibody, a CD38 monoclonal antibody, a CD52 monoclonal antibody, an EGFR inhibitor, a hedgehog pathway inhibitor, a HER2 inhibitor, a histone deacetylase inhibitor, a hormone/antineoplastic, an mitotic inhibitor, an mTOR inhibitor, a multikinase inhibitor, a proteasome inhibitor, a VEGF/VEGFR inhibitor, a biological, an antitoxin, an antivenom, a hematopoietic stem cell mobilizer, an in vivo diagnostic biological, a recombinant human erythropoietin, a cardiovascular agent, an agent for hypertensive emergencies, an agent for pulmonary hypertension, an aldosterone receptor antagonist, an angiotensin a converting enzyme inhibitor, an angiotensin receptor blocker, a neprilysin inhibitor, an antiadrenergic agent, a centrally acting antiadrenergic agent, a peripherally acting agent, an antianginal agent, an antiarrhythmic agent, a group I antiarrhythmic, a group II antiarrhythmic, a group III antiarrhythmic, a group IV antiarrhythmic, a group V antiarrhythmic, an anticholinergic chronotropic agent, an antihypertensive agent, an ACE inhibitor with calcium channel blocking agents, an ACE inhibitor with a thiazide, an angiotensin II inhibitor with calcium channel blockers, an angiotensin II inhibitor with a thiazide, an antiadrenergic agent (central) with a thiazide, an antiadrenergic agent (peripheral) with a thiazide, a beta blocker with a thiazide, a potassium sparing diuretic with a thiazide, a beta-adrenergic blocking agent, a cardioselective beta blocker, a non-cardioselective beta blocker, a calcium channel blocking agent, a catecholamine, a diuretic, a carbonic anhydrase inhibitor, a loop diuretic, a potassium-sparing diuretic, a thiazide diuretic, an inotropic agent, a peripheral vasodilator, a renin inhibitor, a sclerosing agent, a vasodilator, a vasopressin antagonist, a vasopressor, a central nervous system agent, an analgesic, an antimigraine agent, a cox-2 inhibitor, a narcotic analgesic, a nonsteroidal anti-inflammatory agent, a salicylate, an anorexiant, an anticonvulsant, an AMPA receptor antagonist, a barbiturate anticonvulsant, a benzodiazepine anticonvulsant, a carbamate anticonvulsant, a carbonic anhydrase inhibitor anticonvulsant, a dibenzazepine anticonvulsant, a fatty acid derivative anticonvulsant, a gamma-aminobutyric acid analog, a gamma-aminobutyric acid reuptake inhibitor, a hydantoin anticonvulsant, a neuronal potassium channel opener, an oxazolidinedione anticonvulsant, a pyrrolidine anticonvulsant, an succinimide anticonvulsant, a triazine anticonvulsant, an antiemetic/antivertigo agent, a 5HT3 receptor antagonist, an anticholinergic antiemetic, a NK1 receptor antagonist, a phenothiazine antiemetic, an antiParkinson agent, an anticholinergic antiParkinson agent, a dopaminergic antiParkinsonism agent, an anxiolytic, a sedative, a hypnotic barbiturate, a benzodiazepine, a sedative, a cholinergic agonist, a cholinesterase inhibitor, a CNS stimulant, drugs used in alcohol dependence, an anesthetic, a muscle relaxant, a neuromuscular blocking agent, a skeletal muscle relaxant, a coagulation modifier, an anticoagulant reversal agent, an anticoagulant, a coumarin, an indandione, a factor Xa inhibitor, a heparin, a thrombin inhibitor, an antiplatelet agent, a glycoprotein platelet inhibitor, a platelet aggregation inhibitor, protease-activated receptor-1 antagonist, a heparin antagonist, a platelet-stimulating agent, a thrombolytic, a hormone, a 5-alpha-reductase inhibitor, an adrenal corticosteroid, a corticotropin, a glucocorticoid, a mineralocorticoid, an adrenal corticosteroid inhibitor, an antiandrogen, an antidiuretic hormone, an antigonadotropic agent, an antithyroid agent, an aromatase inhibitor, a calcitonin, an estrogen receptor antagonist, a gonadotropin-releasing hormone antagonist, a growth hormone receptor blocker, a growth hormone, an insulin-like growth factor, a parathyroid hormone and analog, a progesterone receptor modulator, a prolactin inhibitor, a selective estrogen receptor modulator, a sex hormone, an androgen, an anabolic steroid, a contraceptive, an estrogen, a gonadotropin releasing hormone, a gonadotropin, a progestin, a somatostatin, a somatostatin analog, a synthetic ovulation stimulant, a thyroid drug, an immunologic agent, an immune globulin, an immunostimulant, a bacterial vaccine, a colony stimulating factor, an interferon, an interleukin, a therapeutic vaccine, a viral vaccine, an immunosuppressive agent, a calcineurin inhibitor, an interleukin inhibitor, a TNF alfa inhibitor, a metabolic agent, an antidiabetic agent, an alpha-glucosidase inhibitor, an amylin analog, a dipeptidyl peptidase 4 inhibitor, an incretin mimetic, an insulin, a meglitinide, a non-sulfonylurea, a SGLT-2 inhibitor, a sulfonylurea, a thiazolidinedione, an antihyperlipidemic agent, a bile acid sequestrant, a cholesterol absorption inhibitor, a fibric acid derivative, a PCSK9 inhibitor, a statin, an antihyperuricemic agent, a bone resorption inhibitor, a bisphosphonate, a bone resorption inhibitor, a CFTR, a CFTR potentiator, a glucose elevating agent, a lysosomal enzyme, a miscellaneous metabolic agent, a peripherally acting anti-obesity agent, a urea cycle disorder agent, an antidote, an antipsoriatic, an antirheumatic, a chelating agent, a cholinergic muscle stimulant, a local anesthetic, including but not limited to ester-based and amide-based anesthetics, a phosphate binder, a psoralen, a smoking cessation agent, a viscosupplementation agent, a nutritional product, a mineral, an electrolyte oral nutritional supplement, a plasma expander, a psychotherapeutic agent, an antidepressant, a monoamine oxidase inhibitor, a phenylpiperazine antidepressant, a selective serotonin reuptake inhibitor, a serotonin-norepinephrine reuptake inhibitor, a tetracyclic antidepressant, a tricyclic antidepressant, an antipsychotic, an atypical antipsychotic, a phenothiazine antipsychotic, a thioxanthene, a radiologic agent, a radiocontrast agent, an iodinated contrast media, an ionic iodinated contrast media, a lymphatic staining agent, a magnetic resonance imaging contrast media, a diagnostic dye, a non-iodinated contrast media, a non-ionic iodinated contrast media, an ultrasound contrast media, a radiologic adjunct, a cardiac stressing agent, a radiologic conjugating agent, a radiopharmaceutical, a diagnostic radiopharmaceutical, a therapeutic radiopharmaceutical, a respiratory agent, an antiasthmatic agent, an antihistamine, an antitussive, a methylxanthine, a decongestant, an expectorant, a leukotriene modifier, a lung surfactants, a respiratory agent, a mast cell stabilizer, a mucolytic, selective phosphodiesterase-4 inhibitor, a mouth and throat product, a nasal preparation, a nasal antihistamine, a decongestant, a nasal lubricant, a nasal steroid, a vitamin, or a CNS active medication, including but not limited to ketamine, glucagon, insulin, nicotine, caffeine, calcitonin, oxytocin, tetrahydrocannabinol (THC), cannabidiol (CBD), or natural cannabis, marijuana, cannabis derivatives or hemp oil, and an opioid or opioid derivative, or combinations thereof.

In one embodiment, the active agent is naloxone, midazolam, ketamine, duloxetine, buprenorphine, morphine, a morphine derivative, fentanyl, a fentanyl derivative, a triptan, a triptan derivative, methadone, a methadone derivative, lidocaine, tetracaine, cocaine, oxycodone, an oxycodone derivative, cisplatin, glucagon, insulin, nicotine, caffeine, ropinirole, calcitonin, oxytocin, a vitamin, tetrahydrocannabinol (THC), cannabidiol (CBD), cannabis, cannabis derivative, hemp oil, clonidine, gabapentin, pregabalin, cyclobenzapine, acetaminophen and acetaminophen derivatives, tramadol, tramadol derivatives, butalbital, butorphanol, meperidine, propoxyphene, levorphanol, nalbuphine, tapentadol or combinations thereof.

The size of the particles can be reduced to nanoparticle size less than 1 nanometer to greater than 2000 nanometers. The particles may be enclosed in liposomes. The foam composition may also be used to deliver stem cells to the brain via the nasal cavity. The foam composition 100 may also enable better hygiene of the nasal cavity by the delivery of both moisturizing and cleaning substances.

The foam composition 100 may include a base solution and can be combined with a gas 20, for example nitrous oxide, or $CO_2$ or air. The resulting foam composition, and as further discussed below, can be generated such that it is sufficient to deliver a desired amount of an active agent e.g., sufficient to deliver at least 50% of an active agent across a blood brain barrier of the subject. The base solution may include the medicine or substance to be delivered and various compositions of water, fat, or other substance, for example, milk or saline, or a combination of two or more.

Other additions to this base solution formula may include various surfactants, foaming agents, stabilizing agents, pH Modifying agents, osmolarity modifying agents, moisturizing agents and preservatives. More modification can be done by adding absorption enhancing agents and variety of other modifying agents.

In one embodiment, the base solution may include the medicine or other substance and 1-99.999% water, by weight. In another example embodiment, the base solution may include the medicine or substance and 1-20% fat, by weight. In yet another example embodiment, the base solution may include the medicine or substance 1-60% by weight. In yet another example embodiment, the base solution may include the medicine or substance and a combination of 10-99% water, by weight and 30-60% fat, by weight. In yet another example embodiment, the base solution may include the medicine or substance or stem cells and a combination of 10-80% water, by weight and 20-60% other substance, by weight. In yet another example embodiment, the base solution may include the medicine or substance or stem cells and a combination of 30-60% fat, by weight and 1-60% other substance/substances, by weight. In yet another example embodiment, the base solution may include the medicine or substance and a combination of 10-99.99% water, by weight, 0.1-60% modifying agents including surfactant, foaming agents, stabilizing agents, osmolarity modifying agents, drug absorption enhancer agents fat and 0.1-60% other substance/substances, by weight.

Stabilizing agents include, but are not limited to xanthan gum, guar gum, and gelatin.

In one embodiment, the base solution may include the medicine or other substance and 10-80% water, by weight. In another embodiment, the base solution may include the medicine or substance and 30-60% fat, by weight. In yet another embodiment, the base solution may include the medicine or substance and 20-60% milk, by weight. In yet another embodiment, the base solution may include the medicine or substance and a combination of 10-80% water, by weight and 30-60% fat, by weight. In yet another embodiment, the base solution may include the medicine or substance and a combination of 10-80% water, by weight and 20-60% milk, by weight. In yet another embodiment, the base solution may include the medicine or substance and a combination of 30-60% fat, by weight, and 20-60% milk, by weight. In yet another embodiment, the base solution may include the medicine or substance and a combination of 10-80%water, by weight, 30-60% fat, by weight, and 20-60% milk, by weight.

The foaming agent may include several available agents. The foaming agents can be a single surfactant or mix of several surfactants and may include, for example, various compositions of sodium lauryl ether sulfate (SLES), sodium lauryl sulfate (also known as sodium dodecyl sulfate or SDS), ammonium lauryl sulfate (ALS), lecithin, glycerol, TWEEN 20 and TWEEN 80. The foam composition 100 may have an acidic neutral or alkaline pH. In addition, it may be preferable that the foam composition be made of natural substances such as what has been described; however, in alternative embodiments, mucosal-compatible synthetic substances may be used.

In one embodiment, the composition is aerated to form a foam by 1) dissolving a carbonate into the composition to form carbonate ions and 2) dissolving a proton donor into the solution to release $CO_2$ gas and form the foam. The carbonate is may be sodium bicarbonate, calcium carbonate, or potassium bicarbonate. The proton donor may be an acid selected from the group consisting of amino acids, carbonic acid, and acetic acid.

In one embodiment, the composition for cleansing or moisturizing a nasal cavity of a subject is a foamable saline solution. The saline solution may be a sterile, normal saline solution. In other embodiments, the saline solution is hypertonic or hypotonic. The saline solution can include one or more other components such as a foaming agent, a pH modifying agent, an osmolarity modifying agent, a stabilizing agent, a moisturizing agent, or a preservative.

In certain embodiments, at least 1%, at least 5%, at least 10%, at least 20%, at least 30%, at least 40%, at least 50%, at least 60%, at least 70%, at least 80%, at least 90% or at least 95% of the active agent crosses the blood brain barrier. In one embodiment, the foam compositions have a longer contact period with the nasal cavity compared to the corresponding dry or liquid solutions.

Figure 3:
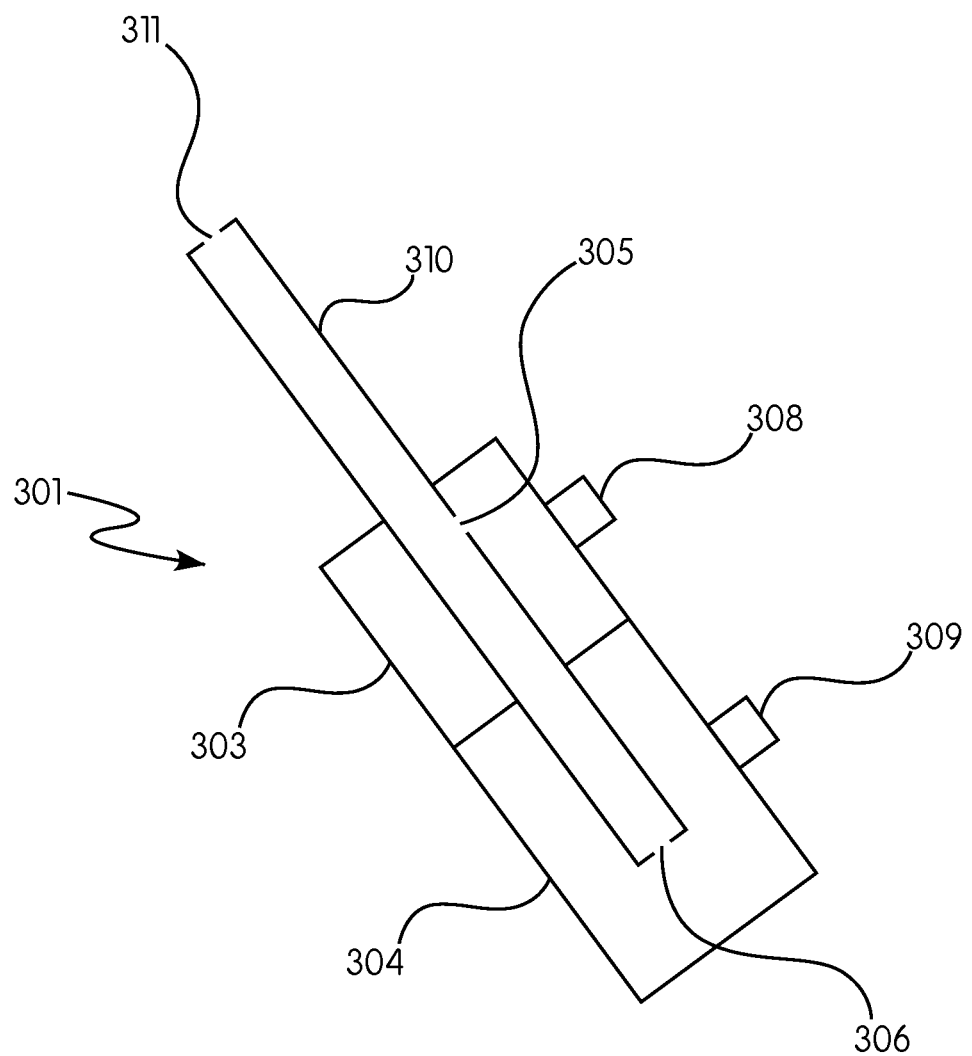
FIG. 3 illustrates a schematic cross-sectional view of an exemplary device to deliver foam to the nasal cavity in accordance with an aspect of the present invention.

FIG. 3 shows an embodiment of a device for delivering foam to the cribriform plate wherein the foam is produced within the device. In one embodiment, the delivery device 301 comprises a composition chamber 303 which can contain a biologically active composition or a saline solution, a gas chamber 304, a composition inlet 305, a gas inlet 306, a composition ejector 308, a gas ejector 309, a tube 310 and a foam outlet 311. In one embodiment, the subject releases the composition using the composition ejector 308 and releases a jet of gas using the gas ejector 309 which pushes the foam into the nose and directs it to the cribriform plate. In other embodiments, the foam and gas are premixed. The delivery device can be made of various materials such as metal, glass or plastic. The tube 310 can be bendable and the device can be held in any direction.

Figure 4A:
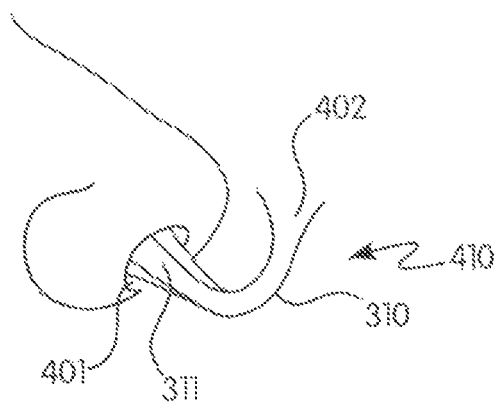
FIGS. 4A-4C illustrate an exemplary use of a device in accordance with an aspect of the present invention.
Figure 4B:
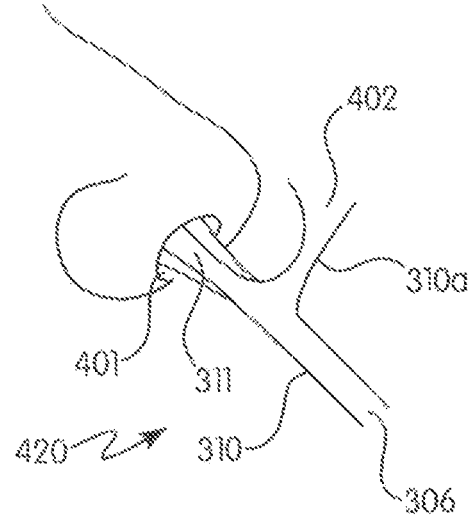
Figure 4C:
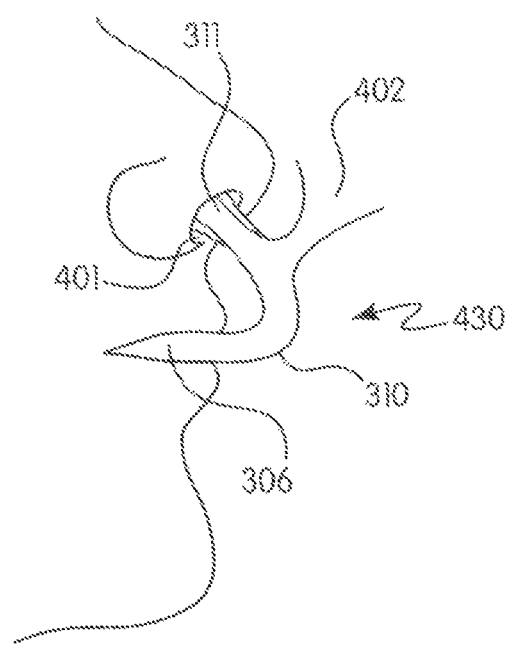

The active agent can be delivered to the cribriform plate by sniffing the foam composition, i.e., forceful inhalation. FIGS. 4A-4C illustrate a subject using various foam delivery devices. FIG. 4A shows a delivery device 410 inserted in a nostril 401 wherein the person inhales through the nose, i.e., sniffs, to draw the foam from the foam inlet 401, through the tube 310 and through the foam outlet 311 such that the foam reaches the cribriform plate. In one embodiment, the foam substantially fills the nasal cavity. FIG. 4B shows a delivery device 420 inserted in a nostril 401 comprising a foam inlet 402, gas inlet 306, foam tube 310a, tube 310 and foam outlet 311. Foam can enter the device by various means, for example, the foam inlet can be attached to a vesicle containing foam or a funnel through which foam is delivered. The gas inlet 306 can be attached to various means for delivering a gas, including but not limited to a gas canister, rubber bulb or syringe. FIG. 4C shows a delivery device 430 wherein the foam outlet 311 is inserted into a nostril 401 and the gas inlet 306 is inserted into the subject's mouth so that the subject can exhale into the tube 310 and force the foam from the foam inlet 402 through the tube 310 to the foam outlet 311. The foam outlet 311 can have a rounded or bulbous ending for ease of insertion and comfort of the subject.

It will be appreciated by those skilled in the art that changes could be made to the embodiments described above without departing from the broad inventive concept thereof. For example, additional components and steps can be added to the various delivery devices or methods of delivery. It is to be understood, therefore, that this invention is not limited to the particular embodiments disclosed, but it is intended to cover modifications within the spirit and scope of the present invention as defined by the appended claims.

I claim:

1. A method for delivering a biologically active foam pharmaceutical composition to a cribriform plate of a nasal cavity of a subject, comprising:
   generating a biologically active foam pharmaceutical composition sufficient to deliver an active agent to the brain without passing through the blood brain barrier of the subject, wherein the biologically active foam pharmaceutical composition comprises:
      i) at least one active agent, and
      ii) a stabilizing agent; and
   filling the entire nasal cavity of the subject with the biologically active foam pharmaceutical composition, thereby delivering the biologically active foam pharmaceutical composition to the brain of the subject,
wherein the filling occurs by forcing, through inhalation or expiration, the foam pharmaceutical composition through a foam outlet in the nostril of the subject and the foam does not pass through an elongated tube to the cribriform plate.

2. The method of claim 1, wherein the active agent is selected from a stem cell, an antimicrobial agent, an antineoplastic agent, an antiarrhythmic agent, an antihypertensive agent, an analgesic agent, anti-inflammatory agent, an anticonvulsant, an anti-Parkinson's agent, a sedative, a muscle relaxant, an anticoagulant, a hormone modulator, an immunosuppressive agent, a metabolic agent, an anesthetic, a nutritional supplement, an antidepressant, a radiologic agent, or an antimigraine agent.

3. The method of claim 1, wherein the stabilizing agent is at least one selected from xanthan gum, guar gum, or gelatin.

4. A method of treating a drug overdose in a subject, comprising generating a biologically active foam pharmaceutical composition sufficient to deliver a naloxone to the brain without passing through the blood brain barrier of the subject, wherein the biologically active foam pharmaceutical composition comprises:
   i) naloxone, and
   ii) a stabilizing agent; and
   filling the entire nasal cavity of the subject with the biologically active foam pharmaceutical composition, thereby delivering the biologically active foam pharmaceutical composition to the brain of the subject,
wherein the filling occurs by forcing, through inhalation or expiration, the foam pharmaceutical composition through a foam outlet in the nostril of the subject and the foam does not pass through an elongated tube to the cribriform plate.

5. The method according to claim 1, wherein the filling occurs by forceful inhalation.

6. The method according to claim 1, wherein the filling occurs by
   inserting a foam outlet of a delivery device into a nostril of the subject, wherein the delivery device comprises the foam outlet and a foam inlet, and
   inhaling through the nose to draw the foam from the foam inlet through the foam outlet and fill the entire nasal cavity of the subject with the biologically active foam pharmaceutical composition.

7. The method according to claim 1, wherein the filling occurs by
   inserting a foam outlet of a delivery device into a nostril of the subject, wherein the delivery device comprises the foam outlet, a foam inlet, and a gas inlet;
   inserting the gas inlet into the mouth of the subject; and
   exhaling through the mouth to force the the foam from the foam inlet through the foam outlet and fill the entire nasal cavity of the subject with the biologically active foam pharmaceutical composition.

8. The method according to claim 1, wherein the active agent is a medication used to treat drug overdose or addition.

9. The method according to claim 8, wherein said active agent is naloxone.

* * * * *